US005654491A

United States Patent [19]
Goetsch et al.

[11] Patent Number: 5,654,491
[45] Date of Patent: Aug. 5, 1997

[54] PROCESS FOR THE PARTIAL OXIDATION OF ALKANES

[75] Inventors: Duane A. Goetsch, Andover; Lanny D. Schmidt, Minneapolis, both of Minn.

[73] Assignee: Regents of the University of Minnesota, Minneapolis, Minn.

[21] Appl. No.: 598,920

[22] Filed: Feb. 9, 1996

[51] Int. Cl.$^6$ .................................................. C07C 27/10
[52] U.S. Cl. ........................................ 568/469.9; 568/451
[58] Field of Search ............................................ 568/469.9

[56] References Cited

U.S. PATENT DOCUMENTS

| | | | |
|---|---|---|---|
| 4,844,837 | 7/1989 | Heck et al. | 252/373 |
| 5,149,464 | 9/1992 | Green et al. | 252/373 |
| 5,382,741 | 1/1995 | Astbury et al. | 585/652 |

FOREIGN PATENT DOCUMENTS

| | | | |
|---|---|---|---|
| 0 303 438 | 2/1989 | European Pat. Off. | C01B 3/38 |
| 0 640 559 | 3/1995 | European Pat. Off. | C01B 3/38 |
| WO90/06282 | 6/1990 | WIPO | C01B 3/38 |
| WO90/06297 | 6/1990 | WIPO | C07C 31/04 |

OTHER PUBLICATIONS

Hickman et al., "Synthesis Gas Formation by Direct Oxidation of Methan over Pt Monoliths," *J. of Catalysis*, 138, 267–282 (1992).
Hickman et al., "Synthesis gas formation by direct oxidation of methane over Rh monoliths," *Catalysis Letters*, 17, 223–237 (1993).
Hickman et al., "Steps in CH$_4$ Oxidation on Pt and Rh Surfaces: High–Temperature Reactor Simulations," *AIChE Journal*, 39(7), 1164–1177 (1993).
Hickman et al., "Production of Syngas by Direct Catalytic Oxidation of Methane," *Science*, 259, 343–346 (1993).
Hochmuth et al., "Catalytic partial oxidation of methane over a monolith supported catalyst," *Applied Catalysts B: Environmental*, 1(2) (1992).
Huff et al., "Ethylene Formation by Oxidative Dehydrogenation of Ethane over Monoliths at Very Short Contact Times," *J. Phys. Chem.*, 97, 11815–11822 (1993).
Huff et al., "Oxidative Dehydrogenation of Isobutane over Monoliths at Short Contact Times," *J. of Catalysts*, 155, 82–94 (1995).
Kung, "Oxidative Dehydrogenation of Light (C$_2$ toC$_4$) Alkanes," *Advances in Catalysts*, 40, 1–37 (1994).
Lunsford et al., "The Role of Water in Promoting the Oxidative Dehydrogenation of Ethane," *Internat'l J. of Chem. Kinetics*, 26, 921–928 (1994).
Mochida et al., "Catalysis in Coal Liquefaction," *Advances in Catalysts*, 40, 39, 320–325 (1994).
Pfefferle et al., "Catalysis in Combustion," *Catal. Rev.–Sci. Eng.*, 29(2&3), 219–267 (1987).
Vernon et al., "Partial Oxidation of Methan to Synthesis Gas," *Catalysis Letters*, 6 181–186 (1990).
M. Huff and L. D. Schmidt; Journal of Catalysis; 149, 127–141(1994) Sep. 23, 1994.

*Primary Examiner*—Paul J. Killos
*Assistant Examiner*—Sreeni Padmanabhan
*Attorney, Agent, or Firm*—Mueting, Raasch, Gebhardt & Schwappach, P.A.

[57] ABSTRACT

A process for catalytic partial oxidation of a hydrocarbon is provided. The process includes: providing a feed gas mixture comprising an oxygen-containing gas and a hydrocarbon gas comprising one or more normal (C$_2$-C$_4$)alkanes; providing a catalyst structure having a transparency of at least about 40%; and passing the feed gas mixture through the catalyst structure at a rate such that the superficial contact time of the feed gas mixture with the catalyst structure is no greater than about 1000 microseconds to produce an exit gas mixture comprising partial oxidation products.

24 Claims, 5 Drawing Sheets

PROCESS FOR THE PARTIAL OXIDATION OF ALKANES

STATEMENT OF GOVERNMENT RIGHTS

The present invention was made with government support under Grant No. CTS-9311295 awarded by the National Science Foundation. The government has certain rights in the invention.

FIELD OF THE INVENTION

The present invention relates to the field of catalytic oxidation of hydrocarbons. More particularly, the present invention relates to the field of catalytic oxidation of hydrocarbons while controlling complete oxidation and decomposition of oxygenates.

BACKGROUND OF THE INVENTION

There is an abundant supply of lower alkanes (i.e., ($C_1$-$C_4$)alkanes) and relatively few means of converting them to more valuable products. Although natural gas is predominantly $CH_4$, it can also contain up to about 15 mole% $C_2H_6$, $C_3H_8$, and $C_4H_{10}$. Natural gas is currently underutilized primarily due to the difficulties associated with transportation from remote sources. Therefore, much research has been devoted to investigating the conversion of methane to more easily transportable products, such as synthesis gas (i.e., "syngas" or a mixture of CO and $H_2$), via catalytic partial oxidation, which can be represented by the following reaction scheme: $CH_4 + \frac{1}{2}O_2 \rightarrow CO + H_2$. See, for example, Hickman et at., *J. Catal.*, 138, 267–282 (1992), and Hickman et al., *Science*, 259, 343–346 (1993).

Catalytic partial oxidation of hydrocarbons results in gaseous products containing varying amounts of carbon monoxide, carbon dioxide, olefins, and oxygenates (i.e., oxygen-containing compounds) such as formaldehyde, acetaldehyde, acetone, etc. Catalytic partial oxidation processes offer great potential for fast, efficient, and economical conversion of lower alkanes associated with remote sources of natural gas into more valuable liquid fuels and chemicals, such as oxygenates. For example, the partial oxidation of butane is an exothermic reaction and can result in a variety of products, such as formaldehyde, acetaldehyde, and butene. These "intermediates," however, are easily converted to CO, $CO_2$, lower ($C_2$-$C_3$) olefins, and $H_2O$, for example, at high temperatures. Thus, the selective formation of the intermediates, particularly the oxygenates, which are generally more valuable, is difficult to accomplish.

It is particularly desirable to form these more valuable intermediates on a commercial scale using partial oxidation because of the resources it could save. For example, formaldehyde is typically produced by a multistep process, which involves conversion of methane to syngas, the syngas to methanol, and finally the methanol to formaldehyde. This multistep process is relatively expensive. Thus, it would be desirable to develop a less expensive and direct route to the formation of oxygenates such as formaldehyde, for example.

To accomplish this, an important goal of catalytic partial oxidation processes is attaining high surface reaction rates, which decreases the contributions from nonselective homogeneous reactions that can result in complete oxidation and decomposition of oxygenates, for example, and thus allow selective catalytic partial oxidation processes to dominate. Sufficiently high surface reaction rates, with few nonselective homogeneous reactions occurring, are very difficult to achieve.

One means by which high surface reaction rates are achieved is by heating the reactants prior to contacting the catalyst, particularly if the catalyst has a low activity. However, preheating the reactants, such as by conventional heat transport through the walls of a reactor, can produce significant thermal reaction before the reactants contact the catalyst and form the complete oxidation products, not the desired intermediates.

Systems containing porous α-alumina monoliths (e.g., blocks of ceramic foam) coated with high activity catalysts, such as Rh (for syngas) or Pt (for olefins), or metal or metal-coated gauze (e.g., wire screens) 1–10 layers thick, can rapidly heat reactants to the reaction temperature and thereby provide essentially complete conversion of the reactants (i.e., typically $CH_4$ and $O_2$). Residence times of only about $10^{-3}$ second are required in such systems. See, for example, Hickman et al., *Catal. Lett.*, 17, 223–237 (1993); Hickman et at., *Science*, 259, 343–346 (1993); Hickman et al., *AIChE*, 39, 1164–1177 (1993); and Huffet at., *J. Phys. Chem.*, 97, 11815–11821 (1993).

In these systems, the gaseous reactants (i.e., the feed gas stream or feed gas mixture) remain at nearly room temperature until they enter (i.e., contact) the catalyst, at which they are heated rapidly to about 1000° C. by the exothermic oxidation reactions occurring at the catalyst. In such systems, because reaction heat is generated directly on the surface of the catalyst, the feed gas stream temperature rises from about 20° C. to about 1000° C. in less than about $10^{-4}$ second. In contrast, if the feed gas stream is heated by heat transfer through the reactor wall, such a temperature rise would take about 0.1 second.

Although these high mass transfer rates decrease the contributions from nonselective homogeneous reactions that can result in complete oxidation and decomposition of oxygenates, few oxygenates are actually produced using these systems. The major products are typically olefins having fewer carbons than the starting material (i.e., cracked olefins), CO, $CO_2$, and $H_2O$ (the relative amounts depend on the prevalance of the water gas shift reaction).

SUMMARY OF THE INVENTION

The present invention provides a process for catalytic partial oxidation of hydrocarbons. In one aspect of the invention, the process includes the steps of: providing a feed gas mixture comprising an oxygen-containing gas and a hydrocarbon gas comprising one or more normal ($C_2$-$C_4$) alkanes; providing a catalyst structure having a transparency of at least about 40%; passing the feed gas mixture through the catalyst structure at a rate such that the superficial contact time of the feed gas mixture with the catalyst structure is no greater than about 1000 microseconds to produce an exit gas mixture comprising partial oxidation products.

In another aspect of the invention, the process includes: providing a feed gas mixture comprising an oxygen-containing gas, one or more normal ($C_2$-$C_4$) alkanes, and no more than about 50 mole-% (preferably, no more than about 15 mole-%) methane; providing a catalyst structure having a transparency of at least about 40%; passing the feed gas mixture through the catalyst structure at a rate such that the superficial contact time of the feed gas mixture with the catalyst structure is no greater than about 500 microseconds to produce an exit gas mixture comprising oxygenates, CO, and $CO_2$; wherein the carbon selectivity for the oxygenates is at least about 5 mole-% carbon and the total carbon selectivity for CO and $CO_2$ is no more than about 70 mole-% carbon; and separating the partial oxidation products from the exit gas mixture.

In yet another aspect of the invention, the process includes: providing a substantially methane-free feed gas mixture comprising an oxygen-containing gas and one or more normal ($C_2$–$C_4$)alkanes; providing a catalyst structure comprising one layer of about 20–120 mesh gauze of Pt-Rh wire having a diameter of about 25 micrometers to about 2.5 millimeters; passing the feed gas mixture through the catalyst structure at a rate such that the superficial contact time of the feed gas mixture with the catalyst structure is no greater than about 500 microseconds to produce an exit gas mixture comprising oxygenates, CO, and $CO_2$; wherein the carbon selectivity for the oxygenates is at least about 10 mole-% carbon and the total carbon selectivity for CO and $CO_2$ is no more than about 50 mole-% carbon; and separating the partial oxidation products from the exit gas mixture.

Preferably, the exit gas mixture includes formaldehyde. Therefore, in another aspect, the present invention includes a method of producing and removing formaldehyde directly by the partial oxidation of hydrocarbons according to the methods of the present invention.

These and other features and advantages of the methods according to the present invention are presented in the detailed description below.

DETAILED DESCRIPTION OF THE INVENTION

The present invention is directed to a process for the partial oxidation of hydrocarbons (preferably, normal ($C_2$–$C_4$)alkanes, and more preferably, normal butane) to form relatively high concentrations of oxygenates and relatively low concentrations of CO and $CO_2$. A preferred process according to the present invention uses a catalyst structure containing one or more Group VIII metals (i.e., Groups 8, 9, and 10) to partially oxidize normal ($C_2$–$C_4$) alkanes associated with remote sources of natural gas into more valuable liquid fuels and chemicals, such as oxygenates.

Significantly, the process of the present invention provides a simple, more controllable, and direct procedure (i.e., a one-step procedure) for the production of relatively high carbon selectivities (e.g., as much as 40 mole-%) of valuable oxygenate commodities such as formaldehyde in the gas phase. Generally, most conventional processes for the production of formaldehyde are gas phase multi-step processes, whereas alternative liquid phase processes are known that are carried out under supercritical conditions, which make it very difficult to control homogeneous reactions.

Figure 1:
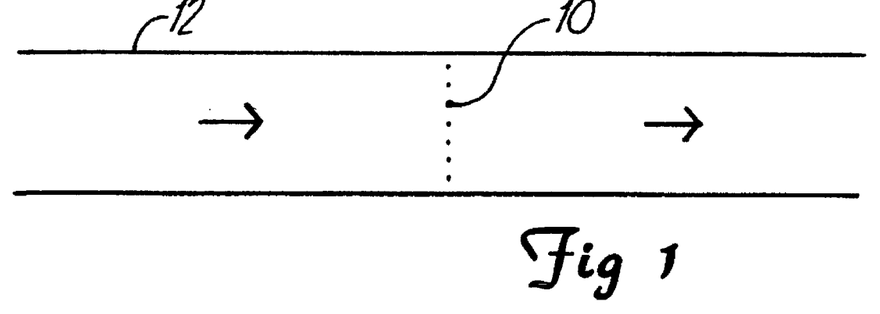
FIG. 1 is a schematic diagram of an apparatus used in a process according to the present invention.

A system according to the present invention is schematically illustrated in FIG. 1. The system includes catalyst structure 10 located in pipe 12 or similar object through which the feed gas stream can flow. Catalyst structure 10 is preferably located in the feed gas stream at an orientation that is transverse to the flow direction.

An important characteristic of catalyst structure 10 is its "transparency." For the purposes of the present invention, transparency is defined in terms of the area of a two-dimensional projection or photograph (e.g., optical or scanning electron microscope photo) of structure 10. It is the ratio of the amount of open area in structure 10 when viewed along the direction of feed gas flow through structure 10 to the total area of catalyst structure 10. It is preferred that catalyst structures 10 according to the present invention have a transparency of at least about 40%. Preferably, the transparency of catalyst structure 10 is at least about 60%, and more preferably at least about 80%. In contrast, a three-dimensional metal coated ceramic foam monolith typically has a transparency of about 5% or less.

Figure 2:
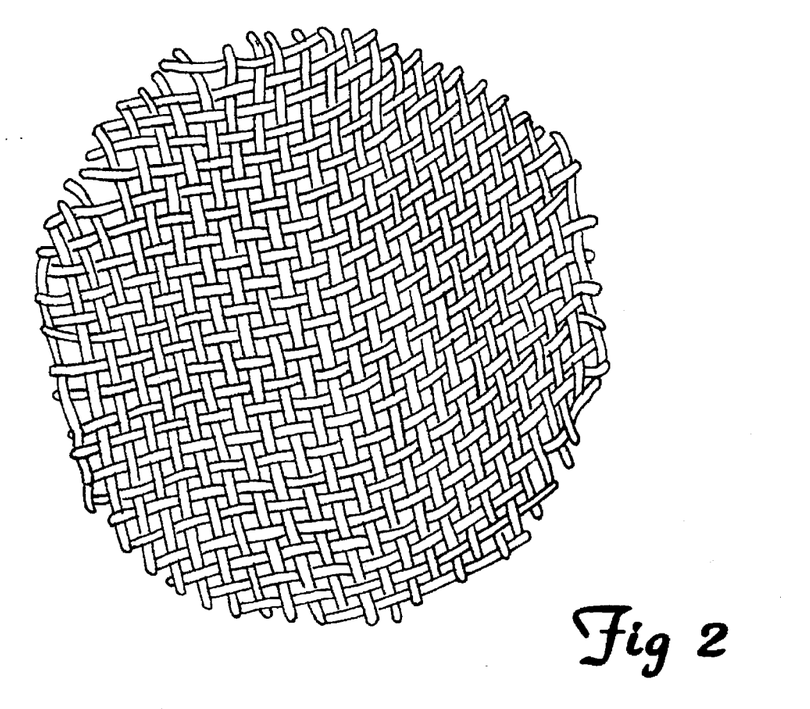
FIG. 2 is a schematic depiction of one embodiment of a catalyst structure comprising a single layer of gauze.

One embodiment of catalyst structure 10 according to the present invention comprises gauze 20 as depicted in FIG. 2. Gauze 20 is preferably a flexible woven metal-containing or metal-coated about 20–120 mesh screen or gauze that is substantially planar. More preferably, it is a gauze of metal wires about 25 micrometers to about 2.5 millimeters in diameter, which are made of about 87–93% by weight (wt-%) Pt and about 7–13 wt-% Rh. The area between the wires is used to calculate the percent transparency of gauze 20 as a function of its entire surface area.

Alternative catalyst structures 10 (FIG. 1) could include a disk with multiple perforations formed therethrough, a honeycomb-like structure, an etched foil and any other structure that provides the desired amount of transparency to effect the partial oxidation of alkanes as discussed below.

A particularly suitable gauze 20 (FIG. 2) according to the present invention is an 80 mesh Pt-Rh alloy gauze (76.2 micrometer diameter) such as that used commercially for $NH_3$ oxidation and for HCN synthesis, which is available from Johnson Matthey, Ward Hill, Mass. This particular gauze has a transparency of about 80% determined by measuring the open area between the wires relative to the total area of the gauze in an optical photograph of the gauze.

Catalyst structure 10 can consist of one or more layers of the gauze in intimate contact as long as the overall transparency of all of the layers (as opposed to each individual layer) is at least about 40%. This can occur if each layer of gauze is lined up with the other layers of gauze. This alignment is difficult to accomplish in practice. Thus, the Pt-Rh gauze catalyst typically consists of one layer of gauze, and preferably only one layer of gauze.

Figure 3A:
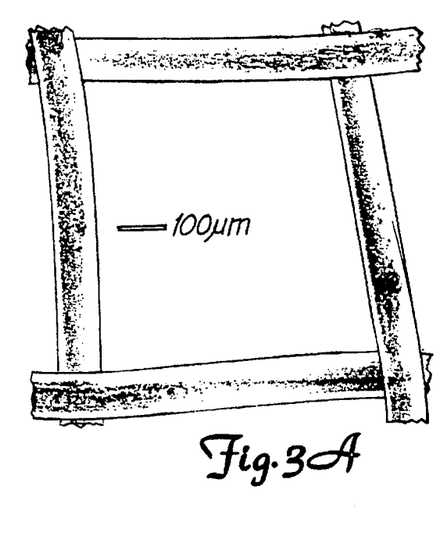
FIG. 3A is an enlarged view of the gauze of FIG. 2 before activation by a feed gas stream.
Figure 3B:
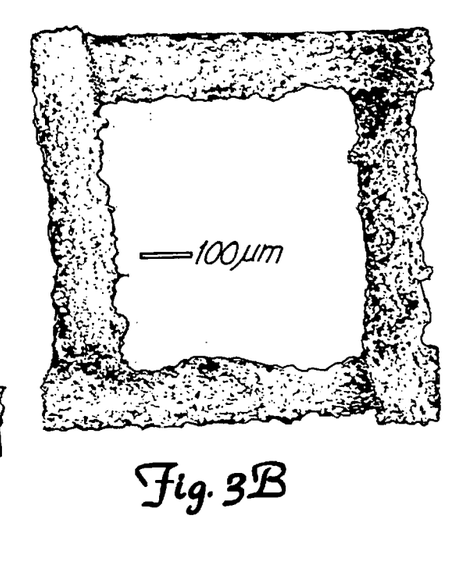
FIG. 3B is an enlarged view of the gauze of FIG. 2 after activation by a feed gas stream using the same magnification as in FIG. 3A.
Figure 3C:
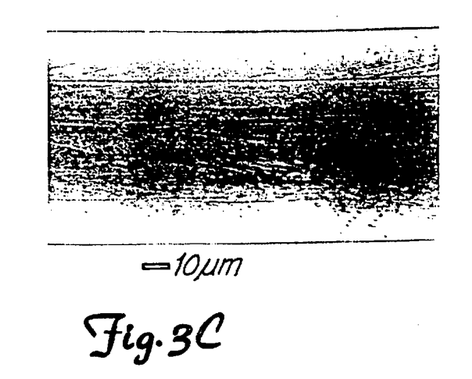
FIG. 3C is an enlarged view of one strand in the gauze of FIG. 2 before activation by a feed gas stream.

As Pt-Rh gauze 20 is used in the process of the present invention, the surface roughens and the diameter of each wire increases by about 10–20%. Scanning electron micrographs reveal that the surface of gauze 10 is smooth before being used in the process according to the present invention (see FIGS. 3A and 3C). The surface of each wire in gauze 20 roughens significantly upon exposure to partial oxidation conditions as shown in FIGS. 3B and 3D.

Figure 3D:
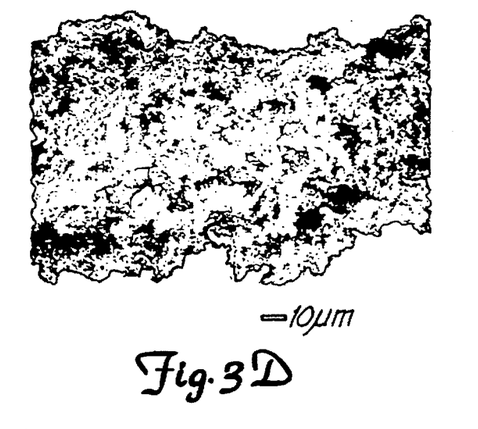
FIG. 3D is an enlarged view of one strand in the gauze of FIG. 2 after activation by a feed gas stream using the same magnification as in FIG. 3A.

Although not intending to be limiting, it is believed that this roughness is due to a restructuring of the metal and formation of metal facets (best seen in FIG. 3D). However it is formed, the roughened, faceted wire surface is believed to promote mixing in the boundary layer, improve mass transport between gas and surface, and enhance mixing between hot and cold gases. This roughness is not deposited carbon, which can typically "kill" the catalyst used in the process of the present invention.

Because this toughening of the surface of the catalyst structure occurs under the conditions of the present invention over time, and not simply upon heating in an inert atmosphere, the alkane conversion and the oxygenate selectivity change as the structure time in the feed gas stream increases. When Pt-Rh gauze 20 is used, the time before equilibrium is established is generally about 40–60 hours, and usually about 50 hours. After a new structure 10 provides steady conversions and selectivities it is referred to as "activated."

The feed gas stream (i.e., feed gas mixture) consists of an oxygen-containing gas (preferably, $O_2$) and a hydrocarbon gas. Preferably, the hydrocarbon gas includes one or more normal ($C_2$–$C_4$)alkanes (more preferably, normal butane). Although the hydrocarbon gas can include a minor amount of methane (i.e., no more than about 50 mole-%, preferably, no more than about 15 mole-%), it is particularly desirable if the hydrocarbon gas (and therefore, the feed gas mixture) is substantially methane free. Water can also be included in the feed gas stream if desired.

The molar ratio of the number of carbon atoms in the alkane to number of oxygen atoms in the oxygen-containing gas in the feed gas stream is greater than about 1:1, preferably greater than about 2:1. This enhances intramolecular vs. intermolecular interactions. That is, it reduces the interaction between hydrocarbon radicals and oxygen. If the ratio is too high, however, the reaction extinguishes. The actual ratio that causes extinction, however, depends on the composition of the feed gas stream. For example, for $C_4H_{10}$ and $O_2$, the reaction extinguishes above a 9.5:1 C:O molar ratio (i.e., a 4.25:1 $C_4H_{10}$:$O_2$ molar ratio).

Partial oxidation of a gas stream of $O_2$ and one or more normal ($C_2$–$C_4$) alkanes over an activated catalyst structure 10 having greater than 40% transparency preferably yields at least about 70% (more preferably, at least about 80%, and most preferably, at least about 90%) conversion of the $O_2$, and high carbon selectivity (preferably, at least about 50%, more preferably, at least about 60%, and most preferably, at least about 70% selectivity) to partial oxidation products (i.e., olefins and oxygenates). The conversion percentages are mole percents based on the total amount of oxygen in the feed gas mixture. The selectivity percentages are mole percents on a carbon basis (calculated as moles product/ moles material converted x moles carbon in product/moles carbon in material converted).

Significantly, these partial oxidation products include relatively large concentrations of the parent olefin (i.e., the noncracked olefin, such as butylene from butane) and oxygenates, and relatively small concentrations of the cracked products (i.e., lower olefins, such as ethylene from butane). Preferably, the carbon selectivity for the parent olefin (e.g., butylene from butane), is at least about 10 mole-% carbon (more preferably, at least about 15 mole-% carbon, and most preferably, at least about 20 mole-% carbon). Preferably, the carbon selectivity for the oxygenates (e.g., formaldehyde, acetaldehyde, acetone, methanol, methyl ethyl ketone, methyl vinyl ketone, butanal, etc.) is at least about 5 mole-% carbon (more preferably, at least about 10 mole-% carbon, and most preferably, at least about 20 mole-% carbon, and in certain particularly preferred embodiments of the present invention, at least about 30 mole-% carbon).

In contrast, although processes using a Pt on ceramic foam monolith (having 5% transparency) or a Pt-Rh gauze catalyst comprising five randomly-oriented layers of the gauze similar to the single layer depicted in FIG. 2 (having only about 13% transparency) give roughly the same amount of partial oxidation products as the process of the present invention, these products are almost exclusively olefins from cracking reactions with less than about 15% (and often only a trace) of organic molecules containing oxygen atoms (i.e., oxygenates).

It is also significant that the process of the present invention produces a relatively small amount of CO and $CO_2$. Preferably, the carbon selectivity for CO and $CO_2$ is no greater than about 70 mole-% carbon (total CO plus $CO_2$ selectivities), more preferably, no greater than about 50 mole-% carbon, and most preferably, no greater than about 30 mole-% carbon. In contrast, the total carbon selectivity for CO and $CO_2$ in processes for manufacturing syngas, such as those disclosed in EP 0640559, typically is at least about 80 mole-% carbon.

The Pt-Rh gauze 20 described above typically provides different reactivities and selectivities for ethane, propane, and butane. Comparison of carbon atom selectivities shows that olefin selectivity strongly decreases while oxygenate selectivity increases with alkyl chain length. Surprisingly, about 40% of reacted butane is converted to oxygen-containing hydrocarbons (i.e., oxygenates), the majority of which is formaldehyde and acetaldehyde, whereas, only 9% of reacted propane is converted to oxygenates.

The Pt-Rh catalyst structure used in the process of the present invention is operated at a temperature of at least about 700° C., preferably within a range of about 800°–1000° C. Temperatures greater than about 1000° C. typically do not allow for fast enough quenching, which leads to a reduction in the yield of the oxygenates.

Typically, the catalyst structure is heated as a result of the exothermic chemical reactions occurring at its surface; however, it can be heated by external means (e.g., electrical resistance, magnetic induction, RF, etc.). Heating by external means can allow for increases in the rate at which feed gas can be passed through the catalyst structure while still obtaining desirable reaction products. In many cases it is helpful to, at a minimum, heat the catalyst structure 10 with external means at the start of the process to begin the exothermic reactions on the catalyst structure. That heating can be accomplished in any suitable manner including electrical resistance, magnetic induction, RF, etc.

The feed gas stream is preferably at room temperature (i.e., 20°–30° C.) prior to contact with the catalyst. Preheating the feed gas stream can cause homogeneous reactions and reduce the selectivity of the process of the present invention for oxygenates. Therefore, preheating the feed gas mixture is not desired, although in some applications preheating the feed gas mixture up to about 300° C. can be tolerated.

That portion of the feed gas stream that contacts catalyst structure 10 is heated very quickly to promote fast reaction rates. Preferably, the system is run nearly adiabatically (i.e., without loss of heat) to reduce the formation of carbon (e.g., coke) on the surface of the gauze catalyst. A significant portion of the feed gas stream does not contact catalyst structure 10 due to the transparency of the structure. As a result, that portion of the feed gas stream does not reach the temperature of the catalyst. Furthermore, the flow rate of the feed gas stream is preferably high enough to prevent significant heating of the portion of the stream not in contact with the catalyst. This unheated portion of the gas stream is available to mix with the hot gases and quench further reaction downstream from the catalyst, thereby leading to production of the desired intermediates.

The feed gas stream velocity past catalyst structure 10 is typically at least about 0.1 meter/second, often as high as 4–5 meters/second, and even as high as 70 meters/second when used in combination with the preferred gauze catalyst structure 20 described above. The maximum velocity will generally determined by the specific equipment used; however, the theoretical limit is that velocity at which the reaction would be extinguished. If an external means of heating the catalyst structure 10 were used, however, this theoretical limit could be significantly large.

Typically, the feed gas stream velocity use with the preferred gauze 20 is within a range of about 0.1–100 meters/second. As a result, the superficial contact time of the feed gas stream with gauze catalyst 20 (wire diameter divided by gas velocity) is less than about 1000 microseconds, and typically within a range of about 1–1000 microseconds. When used with any catalyst structure according to the present invention, it is preferred that the superficial contact time of the feed gas stream with the catalyst be less than about 500 microseconds, more preferably less than about 200 microseconds. As used herein, "superficial contact time" is calculated as the wire diameter divided by the feed gas stream velocity at inlet conditions (i.e., temperature and pressure at the inlet to the reactor). Superficial contact time is inversely proportional to "space velocity" as used in many chemical process descriptions. Space velocity is typically calculated by the following equation:

$$\frac{\text{volume of total feed @ inlet temperature and pressure}}{\text{time} \times \text{volume of the catalyst}}$$

The actual superficial contact time depends on the transparency of the catalyst structure. For example, for a catalyst structure having 80% transparency, the superficial contact time is preferably within a range of about 80–120 microseconds. Furthermore, the superficial contact time can be lowered if the feed gas stream is preheated by external means as described above.

The relatively high transparency (as compared to monoliths) of catalyst structures used in the present invention combined with short superficial contact times (i.e., high space velocities) leads to a significant amount of the feed gas passing through the catalyst structure without contacting the catalyst. That portion of the feed gas stream is not heated to the temperature of the feed gas that contacts the catalyst and react as described above. As a result, reaction products in the wake (i.e., the exit gas mixture or the stream after passing through catalyst structure 10) are rapidly quenched by the relatively cold feed gas stream that by-passes the catalyst. The mixing of the hot, reacted gases (i.e., those that contact catalyst structure 10) and the cold, unreacted gases (i.e., those that pass through catalyst structure 10) occurs shortly after passing through catalyst structure 10. The high oxygen conversion seen in the present invention strongly suggests that significant homogeneous reactions take place in the wake region behind catalyst structure 10, although this is not intended to be limiting.

Where catalyst structure 10 comprises the Pt-Rh gauze 20 described above, that mixing occurs within a few wire diameters downstream of gauze 20. For example, as demonstrated by FIG. 4A, a schematic diagram in enlarged partial cross-section of one gauze catalyst structure depicting the flow of reactants through gauze 20, the portions of the feed gas stream indicated as "A" contacts the wires in the gauze 20. A portion of the feed gas stream (indicated as "B"), however, passes through gauze 20 without contacting the catalyst. That portion, B, of the feed gas stream is not heated by the exothermic reactions occurring at the surface of gauze 20.

Figures 4A, 4B, 5A, 5B:
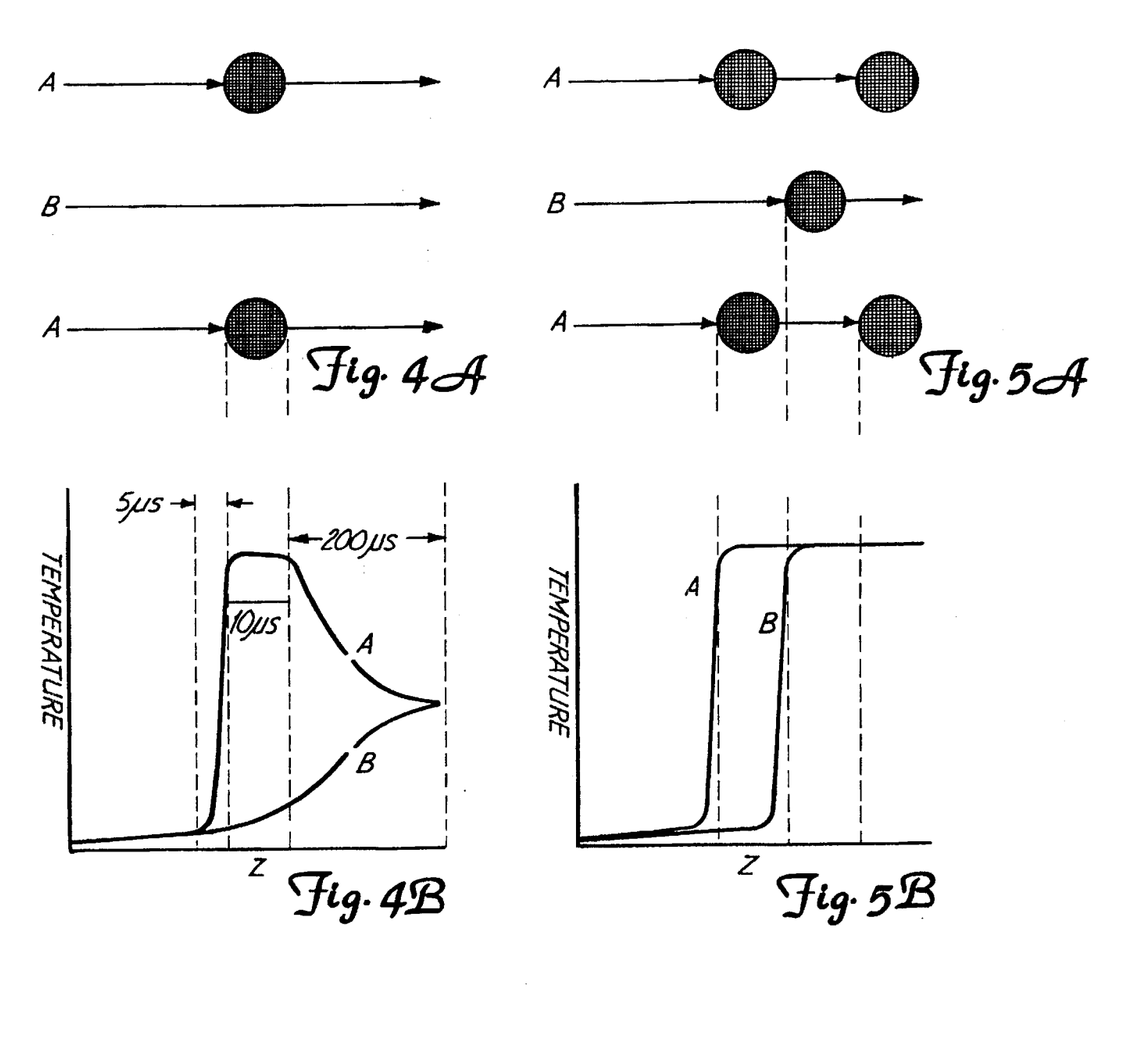
FIG. 4A is a schematic diagram in enlarged partial cross-section of one catalyst structure depicting the flow of reactants through the catalyst structure.
FIG. 4B is a schematic temperature profile of reactant temperature (y-axis) relating to time (x-axis) for reactants passing through the catalyst structure of FIG. 4A.
FIG. 5A is a schematic diagram in enlarged partial cross-section of an alternative catalyst structure depicting the flow of reactants through the catalyst structure.
FIG. 5B is a schematic temperature profile of reactant temperature (y-axis) relating to time (x-axis) for reactants passing through the catalyst structure of FIG. 5A.

During the processes according to the present invention, the temperature of the wires of Pt-Rh gauze catalyst 20 and the portion of the feed gas stream contacting the wires increases to about 700°–1000° C. The portion of the feed gas stream not in contact with the wires, however, mixes with the heated portion of the feed gas stream after the catalyst structure. FIG. 4B is a schematic temperature profile of reactant temperature (y-axis) relating to time (x-axis) for reactants passing through the catalyst structure of FIG. 4A. As shown, portion A of the feed gas stream heats up rapidly to its reaction temperature, remains at near that temperature for the time spent passing through the catalyst structure, and then cools, preferably to approximately half of that temperature (depending on the transparency of the catalyst), in a relatively short period of time. Portion B of the feed gas stream shows a relatively gradual rise in temperature to the point at which both portions A and B are fully mixed and at the same temperature. As a result, the unheated portion B of the feed gas quenches the reactions to produce the desired intermediates.

Where the preferred gauze 20 described above is used as the catalyst structure and the feed gas stream comprising 3.5:.1 $C_4H_{10}$ to $O_2$ at an initial temperature of about 25° C. flows through gauze 20 at a velocity of about 1 meter/second (i.e., superficial contact time of about 100 microseconds), the reaction temperature reached is about 800° C. The mixing between the portions A and B cools the exit gas stream (i.e., the exit gas mixture) to about 400° C. within about 200 microseconds and allows selective production and survival of oxygenates. It is believed that the presence of the parent olefin and oxygenates in the product stream in view of catalyst surface temperatures at greater than about 800° C. is a result of rapidly quenching the temperature using the cold feed gas stream that by-passes the wire surface. Significantly, this cooling occurs without the addition of an external cooling means (e.g., a heat exchanger) or a secondary coolant (e.g., a secondary cold gas or vaporizing liquid).

The rapid quenching of the temperature of the gas stream yields increased concentrations of high value olefins and oxygenates. Such rapid quenching does not occur, however, if catalyst structure 10 has less than about 40% transparency at least in part because an insufficient amount of the feed gas stream passes through catalyst structure 10 without being heated.

For example, decreasing the transparency of catalyst structure 10 to about 13% (using a structure 10 comprising five layers of gauze 20 randomly oriented) increases the olefin selectivity from 36% to 63% (although a significantly lower amount is the parent olefin), but decreases the oxygenate selectivity from 40% to 14%. The exit gas stream temperature from this lower transparency catalyst structure remains at about 800° C. for about 0.2 second, which is about 1000 times the time estimated for a catalyst structure having at least about 80% transparency. It is believed that this produces smaller olefins and alkanes by cracking reactions and oxygenate decomposition.

FIG. 5A schematically depicts a catalyst structure in which the transparency is significantly lower than 40%. Because of the lower transparency, the portion B of the feed gas stream is depicted as also contacting a wire in the catalyst structure. As a result, portion B is also heated as depicted in the temperature profile of FIG. 5B. Because both portions A and B of the feed gas stream are heated, the product gas stream does not experience any significant cooling due to mixing between heated and unheated portions after passing through the catalyst structure. The result, of course, is that the product gas stream has a composition similar to that seen if the feed gas stream were passed through a monolith structure.

One potentially important application of this technology is in the use of a Pt-Rh catalyst structure 10 to provide chemical preheat for catalytic partial oxidation on oxide catalysts such as $V_2O_5$. These catalysts have the potential to produce partial oxidation products, especially organic molecules containing oxygen, with high selectivity. However, their ignition temperatures are much higher than for noble metals, and considerable preheat is necessary to attain high conversion and sustain adiabatic operation. Conventional heat exchangers cannot accomplish this in times less than about 0.1 second, and for alkane-oxygen mixtures considerable homogeneous reaction will occur before reactants reach the oxide catalyst surface.

By using catalyst structure 10 according to the present invention (having a transparency of at least about 40%) just before the oxide catalyst, the gases could be preheated in about 10 microseconds from room temperature to the desired reaction temperature. Rapid quenching between the catalyst structure and the oxide monolith would then keep the conversions sufficiently low that both alkane and oxygen remain for reaction on the oxide.

The process of the present invention is particularly advantageous because the rapid chemical heating coupled with rapid quenching by unreacted gases by-passing the catalyst make catalyst structure 10 according to the present invention, particularly catalyst structure 10 comprising a single layer of the Pt-Rh gauze 20 described above, uniquely able to convert alkanes into useful chemicals with high selectivity and conversions at very high temperatures where reaction rates are extremely fast.

Figure 6:
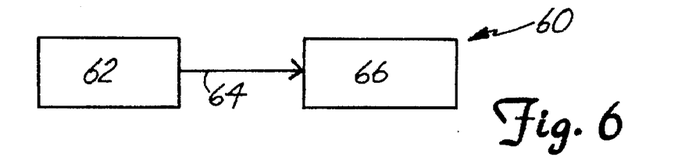
FIG. 6 is a schematic diagram of one system for producing formaldehyde according to the present invention.

As discussed above, one advantageous feature of the present invention is the significant production of formaldehyde in the exit gas stream. FIG. 6 is a schematic depiction of one system 60 employing a reactor 62 in which the methods of selectively producing oxygenates according to the present invention are practiced. That reactor 62 produces an exit gas stream 64 that is directed into a separation means 66 for separating the formaldehyde from the exit gas stream 64. The separation means 66 includes water wash means such as a spray tower or absorber.

The invention will be further described by reference to the following detailed examples. These examples are offered to further illustrate the various specific and illustrative embodiments and techniques. It should be understood, however, that many variations and modifications may be made while remaining within the scope of the present invention.

EXAMPLES

Example 1

The partial oxidation of butane at high oxygen conversion per pass was carried out at 1.4 atm in a plug flow reactor. Butane and oxygen were mixed in ratios of 2:1 to 4.75:1, but more preferably in a 3.5:1 ratio (which was what was used for the data listed in Table I) and fed at 25° C. to the reactor. Initially a 1:1 butane to oxygen ratio was used to begin the reaction and assist in heating the catalyst, which was also preheated with an external source, such as a bunsen burner. Reaction occurring on the catalytic surface heated the surface to about 800° C. and the gases within the boundary layer to temperatures greater than 800° C. The catalyst surface temperature was measured by optical pyrometry. The gas temperature was measured using a K-type thermocouple (iron constantan) in a quartz sleeve placed inside the reactor.

Mixing of hot gases with cold reactants that by-passed the catalyst resulted in homogenous reaction between oxygen and butane. Since homogenous reactions between hydrocarbons and oxygen occur via radical chain branching reactions, reaction occurred until the mixture was cooled by mixing with cold reactant enough such that the rate of chain termination exceeded the rate of chain branching. This rapid quenching effect resulted in gas temperatures of 400° C. in less than 1 millisecond after leaving the catalyst.

In this case, the reactor consisted of a well-insulated 1.8 cm diameter quartz tube that contained a single layer of Pt Rh gauze. However, a more typical reactor would consist of a steel tube lined with ceramic. The gauze consisted of nominal (as purchased) 0.076 mm Pt 10 wt % Rh wire woven to give an 80 mesh gauze with a transparency of 82%. Care was taken to avoid touching and contaminating the gauze, particularly with iron.

The reactants and products were measured by gas chromatography at the reactor inlet and outlet, respectively, using a Hewlett Packard 5890A GC with a Hayesep D30 foot ⅛ inch packed column from Altech, Chicago, Ill., and a TC detector with the following conditions: injection at 170° C.; detector at 170° C.; $Q_{cof}$=50 cm$^3$/minute; and temperature program conditions of $T_i$=30° C., hold 5 minutes, ramp at 10° C. /minute to 150° C., hold 30 minutes, ramp at 2° C. /minute to 210° C., hold 30 minutes; injection at 170° C.

Typical results are shown in Table I (1.4 atm pressure, 7:1 C:O ratio, 260 microseconds superficial contact time). The oxygenates primarily consisted of formaldehyde (approximate carbon selectivity =10%) and acetaldehyde.

Figure 7:
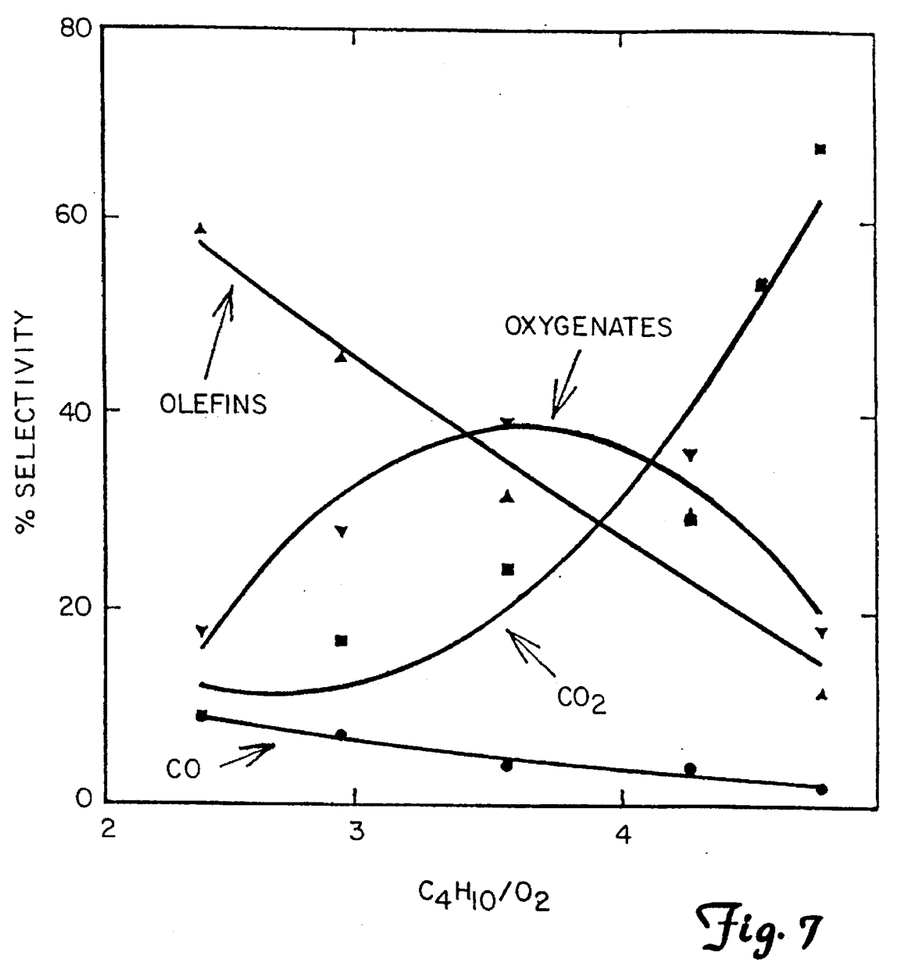
FIG. 7 is a graph depicting the percent selectivity of a method according to the present invention for oxygenates, olefins, $CO_2$, and CO as a function of the feed gas ratio (moles butane to moles oxygen).
Figure 8:
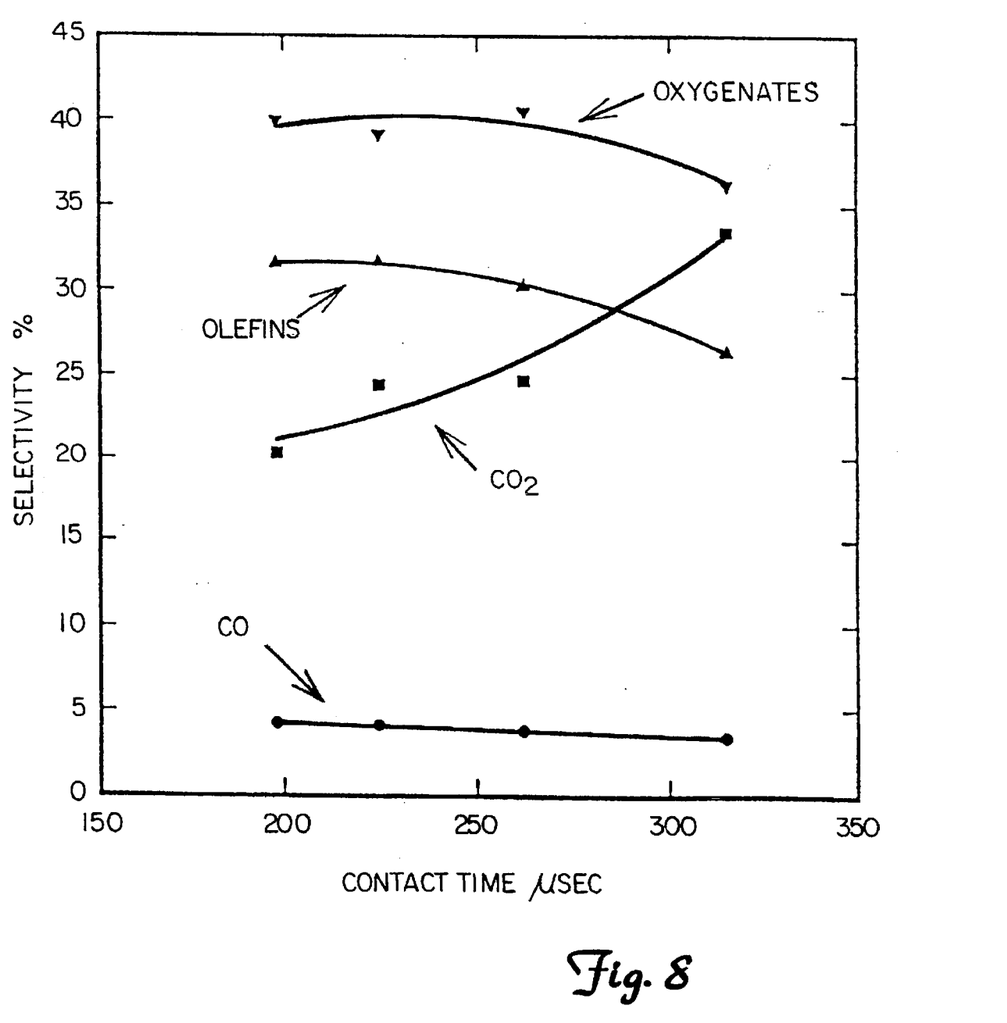
FIG. 8 is a graph depicting the percent selectivity of a method according to the present invention for oxygenates, olefins, $CO_2$, and CO as a function of superficial contact time in microseconds.

FIGS. 7 and 8 give typical results for the partial oxidation of butane over a single Pt-Rh gauze. The conditions used to generate the data in FIG. 7 were 1.4 atm reactor pressure, 7:1 C:O ratio, and 260 microseconds superficial contact time (exit gas temperature not constant). The data in FIG. 7 shows that: (1) a ratio of 3.5:1 $C_4H_{10}:O_2$ (7:1 C:O) is preferred for oxygenate production; (2) $CO_2$ selectivity increases with C:O ratio; (3) at 4.75:1 $C_4H_{10}:O_2$ the reaction extinguishes; and (4) the largest total carbon selectivity for $CO_2$ and CO is about 75 mole-% carbon.

The conditions used to generate the data in FIG. 8 were $C_4H_{10}:O_2$ molar ratio of 3.5:1 (i.e., 7:1 C:O ratio), temperature of the exit gas was constant at 410° C., and a reactor pressure of 1.4 atmospheres. The data in FIG. 8 shows that the ratio of oxygenates to olefins is substantially constant as the superficial contact time varies, which indicates a parallel reaction mechanism.

TABLE I

| 1 layer of Pt Rh Gauze | |
|---|---|
| Conversion, % | |
| Butane | 10 |
| Oxygen | 90 |
| Carbon Selectivity, % | |
| CO | 4 |
| $CO_2$ | 20 |
| $C_4^=$ | 27 |
| $C_2^= + C_3^=$ | 9 |
| Oxygenates | 40 |

Example 2

The partial oxidation of ethane and propane was carried out, and evaluated, in a manner similar to that described in Example 1 (ethane or propane to oxygen ratio of 7:1 C:O, feed gas temperature at 25° C., catalyst surface temperature of about 900° C. for ethane and 850° C. for propane, exit gas temperature of about 504° C., and 260 microseconds superficial contact time). The results are shown below in Tables II and III.

TABLE II

| 1 layer of Pt Rh Gauze | |
|---|---|
| Conversion, % | |
| Ethane | 34 |
| Oxygen | 100 |
| Carbon Selectivity, % | |
| CO | 9 |
| $CO_2$ | 9 |
| $CH_4$ | 13 |
| $C_3^=$ | trace |
| $C_2^=$ | 62 |
| Oxygenates | 7 |

TABLE III

| layer of Pt Rh Gauze | |
|---|---|
| Conversion, % | |
| Propane | 16 |
| Oxygen | 99 |
| Carbon Selectivity, % | |
| CO | 6 |
| $CO_2$ | 17 |
| $C_3^=$ | 30 |
| $C_2^=$ | 28 |
| $CH_4$ | 10 |
| Oxygenates | 9 |

Comparative Example A

In this case, the partial oxidation of butane was carried out as in Example 1 except that 5 layers of Pt-Rh gauze were used as the catalyst having a transparency of approximately 13%. In this case, little reactant by-passing of the catalyst occurred and the gas temperature downstream of the catalyst was in excess of 800° C. At these temperatures, desirable oxygenates decompose and olefin formation is the favored reaction pathway. Results obtained appear in Table IV.

TABLE IV

| 5 layers of Pt Rh Gauze | |
|---|---|
| Conversion, % | |
| Butane | 38 |
| Oxygen | 99 |
| Carbon Selectivity, % | |
| CO | 9 |
| $CO_2$ | 9 |
| $C_4^=$ | 15 |
| $C_2^= + C_3^=$ | 48 |
| Oxygenates | 14 |

Comparative Example B

The same reactions described in Example 1 was repeated using Pt supported on a foamed $\alpha$-$Al_2O_3$ monolith. The catalyst was prepared by incipient wetness technique using a solution of $H_2PtCl_6$. A monolith was weighed to determine its mass and the amount of solvent (e.g., water) needed to saturate the monolith was determined. This was done by adding water to the monolith from a graduated buret one drop at a time until the addition of a single drop caused the solution to wet the vessel containing the monolith. This is referred to as incipient wetness. The monolith was then dried in a vacuum oven and calcined at 500° C. for one hour. The appropriate amount of material to be impregnated into the monolith was then measured and added to the amount of water previously determined necessary for incipient wetness. This solution was then added to the calcined monolith. The impregnated monolith was dried at room temperature over night and further dried for 3 hours in a vacuum oven at 100 ° C. Finally, the salt was decomposed by heating the structure under nitrogen to 500° C. The process was repeated until the desired Pt loading was achieved, typically 1 wt-%.

The high transport properties associated with a monolith coupled with its high effective thermal conductivity resulted in rapid heating of the reactant gases minimizing any opportunity for quenching to occur. The high reaction temperature (greater than 950° C.) resulted in little or no oxygenate production. In addition, the olefins that were produced are a result of cracking reactions rather than the more desirable dehydrogenation reaction. Results appear in Table V.

TABLE V

| Pt Coated Monolith | |
|---|---|
| Conversion, % | |
| Butane | 88 |
| Oxygen | 100 |
| Carbon Selectivity, % | |
| CO | 16 |
| $CO_2$ | 7 |
| $CH_4$ | 11 |
| $C_4^=$ | trace |
| $C_2^= + C_3^=$ | 66 |
| Oxygenates | trace |

The complete disclosure of all patents, patent documents, and publications cited herein are incorporated by reference.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A process for catalytic partial oxidation of a hydrocarbon comprising:
   (a) providing a feed gas mixture comprising an oxygen-containing gas and a hydrocarbon gas comprising one or more normal ($C_2$–$C_4$) alkanes;
   (b) providing a metal catalyst structure having a transparency of at least about 40%;
   (c) passing the feed gas mixture through the catalyst structure at a rate such that the superficial contact time of the feed gas mixture with the catalyst structure is no greater than about 1000 microseconds to produce an exit gas mixture comprising partial oxidation products comprising oxygenates.

2. The process of claim 1 wherein the catalyst structure comprises gauze.

3. The process of claim 2 wherein the catalyst structure comprises one layer of gauze.

4. The process of claim 2 wherein the catalyst structure has a transparency of at least about 80%.

5. The process of claim 2 wherein the catalyst structure comprises one or more Group VIII metals.

6. The process of claim 5 wherein the catalyst structure comprises Rh and Pt.

7. The process of claim 1 wherein the hydrocarbon gas comprises normal butane.

8. The process of claim 7 wherein the partial oxidation products comprise butylene.

9. The process of claim 1 wherein the hydrocarbon gas is substantially methane free.

10. The process of claim 1 wherein the exit gas mixture comprises CO and $CO_2$ and the total carbon selectivity for CO and $CO_2$ is no more than about 70 mole-% carbon.

11. The process of claim 1 wherein the carbon selectivity for the oxygenates is at least about 5 mole-% carbon.

12. The process of claim 11 wherein the carbon selectivity for the oxygenates is at least about 20 mole-% carbon.

13. The process of claim 1 wherein the oxygenates comprise formaldehyde.

14. The process of claim 1 wherein the partial oxidation products comprise parent olefins.

15. The process of claim 13 wherein the carbon selectivity for the parent olefins is at least about 10 mole-% carbon.

16. The process of claim 1 wherein the superficial contact time of the feed gas mixture with the catalyst structure is no greater than about 500 microseconds.

17. The process of claim 1 wherein the superficial contact time of the feed gas mixture with the catalyst structure is no greater than about 200 microseconds.

18. A process for catalytic partial oxidation of a hydrocarbon comprising:
   (a) providing a feed gas mixture comprising an oxygen-containing gas, one or more normal ($C_2$–$C_4$)alkanes, and no more than about 50 mole-% methane;
   (b) providing a metal catalyst structure having a transparency of at least about 40%;
   (c) passing the feed gas mixture through the catalyst structure at a rate such that the superficial contact time of the feed gas mixture with the catalyst structure is no greater than about 500 microseconds to produce an exit gas mixture comprising oxygenates, CO, and $CO_2$; wherein the carbon selectivity for the oxygenates is at least about 5 mole-% carbon and the total carbon selectivity for CO and $CO_2$ is no more than about 70 mole-% carbon; and
   (d) separating the oxygenates from the exit gas mixture.

19. The process of claim 17 wherein the carbon selectivity for the oxygenates is at least about 20 mole-% carbon.

20. The process of claim 18 wherein the oxygenates comprise formaldehyde.

21. The process of claim 19 wherein the formaldehyde is separated from the exit gas mixture using a water wash.

22. The process of claim 17 wherein the superficial contact time of the feed gas mixture with the catalyst structure is no greater than about 200 microseconds.

23. The process of claim 17 wherein the hydrocarbon gas comprises butane and the exit gas mixture further comprises butylene, wherein the carbon selectivity for butylene is at least about 10 mole-% carbon.

24. A process for catalytic partial oxidation of a hydrocarbon comprising:
   (a) providing a substantially methane-free feed gas mixture comprising an oxygen-containing gas and one or more normal ($C_2$–$C_4$)alkanes;
   (b) providing a metal catalyst structure comprising one layer of about 20–120 mesh gauze of Pt-Rh wire having a diameter of about 25 micrometers to about 2.5 millimeters;
   (c) passing the feed gas mixture through-the catalyst structure at a rate such that the superficial contact time of the feed gas mixture with the catalyst structure is no greater than about 500 microseconds to produce an exit gas mixture comprising oxygenates, CO, and $CO_2$; wherein the carbon selectivity for the oxygenates is at least about 10 mole-% carbon and the total carbon selectivity for CO and $CO_2$ is no more than about 50 mole-.% carbon; and
   (d) separating the oxygenates from the exit gas mixture.

* * * * *

UNITED STATES PATENT AND TRADEMARK OFFICE
CERTIFICATE OF CORRECTION

PATENT NO.: 5,654,491
DATED: August 5, 1997
INVENTOR(S): Duane A. Goetsch et al.

It is certified that error appears in the above-identified patent and that said Letters Patent is hereby corrected as shown below:

Col. 1, line 30, delete "CO +$H_2$" and insert --CO+$H_2$--;

Col. 1, line 31, delete "et at.," and insert --et al.,--;

Col. 2, line 18, delete "et at.," and insert --et al.,--;

Col. 2, line 19, delete "Huff et at.," and insert --Huff et al.,--;

Col. 5, line 26, delete "toughening" and insert --roughening--;

Col. 11, line 49, delete "layer of" and insert --1 layer of--;

Col. 13, line 48, delete "claim 13" and insert --claim 14--;

Col. 14, line 20, delete "claim 17" and insert --claim 18--;

Col. 14, line 22, delete "claim 18" and insert --claim 19--;

Col. 14, line 24, delete "claim 19" and insert --claim 20--;

UNITED STATES PATENT AND TRADEMARK OFFICE
CERTIFICATE OF CORRECTION

PATENT NO.: 5,654,491
DATED: August 5, 1997
INVENTOR(S): Duane A. Goetsch et al.

It is certified that error appears in the above-identified patent and that said Letters Patent is hereby corrected as shown below:

Col. 14, line 26, delete "claim 17" and insert --claim 18--;

Col. 14, line 30, delete "claim 17" and insert --claim 18--;

Col. 14, line 44, delete "through-the" and insert --through the--; and

Col. 14, line 52, delete "mole-.%" and insert --mole-%--.

Signed and Sealed this

Sixteenth Day of March, 1999

Q. TODD DICKINSON

Attest:

Attesting Officer

Acting Commissioner of Patents and Trademarks